United States Patent [19]

Mayer et al.

[11] Patent Number: 4,467,123
[45] Date of Patent: Aug. 21, 1984

[54] PROCESS FOR THE PREPARATION OF ALKALI METAL DIPHENYLATES AND FREE HYDROXYDIPHENYLS

[75] Inventors: Dietmar Mayer; Horst-Dieter Kramer, both of Leverkusen; Eike Gabel, Bergisch-Gladbach; Wilfried Köhler, Cologne, all of Fed. Rep. of Germany

[73] Assignee: Bayer Aktiengesellschaft, Leverkusen, Fed. Rep. of Germany

[21] Appl. No.: 459,738

[22] Filed: Jan. 20, 1983

[30] Foreign Application Priority Data

Feb. 6, 1982 [DE] Fed. Rep. of Germany ....... 3204079

[51] Int. Cl.$^3$ .................... C07C 37/04; C07C 39/12
[52] U.S. Cl. ................................. 568/730; 568/722
[58] Field of Search .................. 568/722, 730, 738

[56] References Cited

U.S. PATENT DOCUMENTS 4,243,822  1/1981  Demler et al. ................ 568/730

FOREIGN PATENT DOCUMENTS 1108177  7/1954  France ........................ 568/730
 649945  2/1951  United Kingdom ............ 568/730

OTHER PUBLICATIONS

Houben-Weyl: "Methoden der Organischen Chemie", Band 6 DT., Stuttgart, Thieme, 1976, pp. 208 & 209.
Chemical Abstracts, Band 82-Nr. 5, Feb. 3, 1975, Seite 481 Nr. JP-A-74 16417 (Nippon Steel Chemical Co., Ltd.) 4-22-81.
Chemical Abstracts, Band 95, Nr. 11, Sep. 1981 Seite 611 Nr 97365v, Columbus, OH, USA & JP-A-81 57728 (Hodogaya Chemical Co., Ltd.) 5-20-81.
Chemical Abstracts, Band 87, Nr. 19, Nov. 7, 1977, Seite 557, Nr. 151840w, Columbus, Ohio, USA & JP-A-77 68514.
Chemical Abstracts, Band 75, Nr. 25, Dec. 20, 1971, Seite 299, Nr. 151519a, Columbus, Ohio USA & Japan-A-71 30509, (Seitetsu Kagaku Kigay Co., Ltd.) 4—9-71 Insgesamt.
Chemical Abstracts, Band 55, Nr. 10, May 15, 1961, Spalte 9347, Abschnitt e Columbus, Ohio, USA & JP-A-60 08720 (Yoshio Nagai) 7-7-60 Insgesamt.
Chemical Abstracts, Band 81, Nr. 1, Jul. 8, 1974, Seite 287, Nr. 3581y, Columbus, OH, USA & JP-A-74 01541 (Sanko Chem. Co. Ltd.) 8-1-74.

Primary Examiner—Werren B. Lone
Attorney, Agent, or Firm—Sprung, Horn Kramer & Woods

[57] ABSTRACT

Hydroxydiphenyls can be prepared by reacting diphenylsulphonic acids or their alkali metal salts with an alkali metal hydroxide at elevated temperature and elevated pressure, in the presence of water. For this purpose, the diphenylsulphonic acids or their alkali metal salts are reacted, at a temperature between 280° and 330° C. and a pressure of up to 120 bar, with an amount of aqueous alkali metal hydroxide having a concentration of at least 50% by weight, such that, after all acidic groups have been neutralized, 3 to 25 mols of alkali metal hydroxide per equivalent of sulphonate group are present in the reaction mixture. Mineral acids are added to the alkaline reaction mixture, after it has been cooled and diluted with water, until the pH value is less than 8, and the precipitated hydroxydiphenyl is isolated at a temperature from $-5°$ C. to $+100°$ C.

22 Claims, No Drawings

PROCESS FOR THE PREPARATION OF ALKALI METAL DIPHENYLATES AND FREE HYDROXYDIPHENYLS

The present invention relates to a process for the preparation of alkali metal mono- and dihydroxy-diphenylates and free mono- and dihydroxy-diphenyls from the corresponding diphenylsulphonic acids or their salts.

Dihdroxy-diphenyls are used as starting materials for high-grade condensation polymers, such as polycarbonates, polyesters and powder coatings, in particular the property of high-temperature stability being noteworthy (German Offenlegungsschrift No. 3,031,094). Owing to the structural similarity, monohydroxy-diphenyls can be employed as chain terminators for establishing the molecular weights. Dihydroxy-diphenyls are also used as intermediate products for pharmaceutical products, and as stabilizers and antioxidants for rubbers, oils and polymers. 4-Hydroxy-diphenyl-(p-phenyl-phenol) is furthermore used as an intermediate product for the preparation of varnish resins, non-ionic emulsifiers and plant protection agents (Ullmanns Encyclopädie der technischen Chemie (Ullmann's Encylcopaedia of industrial chemistry), 4th edition, volume 18, page 219).

The preparation of 4-hydroxy-diphenyl and 4,4'-dihydroxy-diphenyl from diphenyl-4-sulphonic acid and diphenyl-4,4'-disulphonic acid respectively, with the aid of a molten alkali, the sulpho groups being replaced by the hydroxyl groups, is known. To this molten alkali is added, in many cases, the sodium salts of the stated sulphonic acids, which are obtained after the sulphonation of diphenyl with excess sulphuric acid, dilution of the sulphonation mixture with water, partial neutralisation with sodium hydroxide solution or salting-out with sodium chloride, and subsequent filtration and drying.

For example, the Japanese patent application 71-30,507 may be mentioned, in which 3 to 5 mols of NaOH per SO₃Na group are reacted at a temperature of at least 380° C., at atmospheric pressure. Furthermore, German Offenlegungsschrift No. 3,031,094 may be mentioned, in which the melt reaction, also carried out at atmospheric pressure, is started with 2 to 10 mols of alkali metal hydroxide per sulphonate group, and further sulphonate is then added in an amount such that a total of 2 to 3 mols of alkali metal hydroxide, preferably potassium hydroxide, are present per sulphonate group. A range from 342 to 350° C. is mentioned as the temperature in this reaction.

Some of the processes described require very high temperatures, that is to say are very energy-consumptive, and need special, expensive reactor materials to resist the high thermal stress. The high temperatures also favour the formation of numerous by-products which have a substantial adverse effect on the quality, for example of the 4,4'-dihydroxydiphenyl. Since in most cases a highly pure product is required for the polycondensation purposes mentioned, it is necessary to keep the number and concentration of the impurities formed during the melt reaction as low as possible. Particularly in the case of 4,4'-dihydroxy-diphenyl, the content of monofunctional hydroxy derivatives, owing to their chain-terminating properties, has an adverse effect on the polycondensation reactions.

In order to reduce the reaction times at the high temperatures of the processes described, the more expensive potassium hydroxide, owing to its greater alkalinity, is preferred to sodium hydroxide in many of these processes. Thus, German Offenlegungsschrift No. 3,031,094 already mentioned describes yields of about 85% when KOH is used, and of only 75% when NaOH is used. The use of KOH is also described to British patent specification No. 2,071,090, wherein diphenyl di-potassium sulphonate is heated, under atmospheric pressure, with 4.7 mols of KOH per equivalent of potassium sulphonate group, at 335 to 340° C. for 3 hours and then at 360° C. for a short time.

A further variant for reducing the high temperature in the molten alkali processes described comprises the use of additives which are intended to reduce the melt temperatures and the viscosities of the melts. Thus, U.S. Pat. No. 2,368,361 describes a process for the preparation of monohydroxy- or dihydroxy-diphenyl from the associated sulphonic acid Na salts, in which, in order to convert excess sulphuric acid, benzene is added, directly after the sulphonation of the diphenyl, to form benzenesulphonic acid. This benzenesulphonic acid in the form of its Na salt then serves as a reaction-promoting additive to the molten alkali and is converted into phenol in this reaction, which is then separated off from the hydroxy-diphenyl by distillation. This process is carried out at 350 to 370° C.

In J. Chem. Soc. Japan, Vol. 84, (1963), page 143, a mixed melt of about 0.7 mol of KOH and 0.5 mol of NaOH is initially introduced to produce the molten alkali, in which about 0.056 mol of di-potassium diphenyl disulphonate is added in small portions. The replacement of the sulphonate groups by OH groups is then effected in the melt, at 330° C. under atmospheric pressure. The yield is only 19% after the product has been recrystallized twice.

In Japanese patent application 60-8720, a mixed melt of KOH, NaOH and sodium acetate is initially introduced, in which melt diphenylsulphonic acid Na salt is reacted under atmospheric pressure, at 280 to 300° C.

Yet another variant is described in Japanese Patent application 71-30,508 (quoted according to C.A., Vol. 75 (1971), 151518 z), wherein diphenyl-sulphonic acid Na salt is reacted with NaOH in the presence of o-phenylphenol or its salt, under atmospheric pressure, at 360 to 370° C.

In yet another variant, Japanese patent application 71-30,509 describes the use of various metal phosphates for the conversion of diphenyl-sulphonic acid Na salt into hydroxy-diphenyls. Thus, for example, diphenyl Na sulphonate is converted into crude p-phenyl-phenol in a yield of 98.3 or 98.6%, using a 5-fold molar excess of aqueous 45% strength HaOH in a 5 hour reaction at 380° C., in the presence of 7.8% of sodium phosphate or dipotassium hydrogen phosphate, respectively. If, under otherwise identical conditions, the phosphate additive is omitted, the yield falls to 64.2%, and increases again to 94.5% only when the reaction temperature is increased to 400° C.

Japanese patent application 77-68,154 describes a process in which diphenyl-disulphonic acid Na salt is mixed with approximately 5 mols of NaOH per Na sulphonate group, in the form of 70% strength NaOH, and the mixture is transferred to a stirred vessel, and heated to 330° C. in the course of 6 hours while nitrogen is passed through. The reaction mixture is then kept at this temperature for a further 10 hours. After the mixture has been dissolved in water, and treated with active charcoal for 30 minutes, a dark brown aqueous di-Na salt solution of the dihydroxydiphenyl is obtained, from which, after acidification, a pale brown powdery crystalline product is obtained in 80% yield. This dihydroxy-diphenyl, which is completely unsuitable for polymerization purposes, must, according to the teaching of the Japanese patent application mentioned, be treated with hydrazine or hydrazine compounds.

Attempts have also already been made to carry out the reaction of diphenyl Na sulphonates with aqueous sodium hydroxide solution in such a manner that this water remains in the reaction mixture during the reaction. Thus, Japanese patent application 74-16,417 describes the reaction of diphenyl Na sulphonate with 70% strength NaOH at 400° C. for 1½ hours to give 93.6% of the theoretical yield of crude p-phenylphenol. If this reaction is carried out at 380° C., a yield of only 82.9% is obtained in a reaction lasting 5 hours. When 45% strength NaOH is used, the yield decreases to 68.1% at a reaction temperature of 380° and decreases further to 59.2% at a reaction temperature of 360°. In the conversion of diphenyl Na disulphonate to crude 4,4'-dihydroxy-diphenyl using 70% strength NaOH at 380° C. in a reaction lasting 5 hours, a yield of 22.3% is first obtained; only at a temperature of 440° C. does the yield increase to 96.3%.

Yet another process, as described in Japanese patent application 81-57,728, shows the reaction of diphenyl Na disulphonate with 70% strength sodium hydroxide solution in a reaction lasting 10 hours at 330 to 335° C., while nitrogen is passed through. It is also necessary to purify the crude product obtained in this reaction, the stated Japanese patent application claiming an extraction with 1-heptanol. A yield of 19.5 parts of the crystallized dihydroxyiphenyl is obtained from 53.7 parts of the disulphonate, corresponding to a yield of about 70% of the theoretical yield.

Hence, none of the processes described are satisfactory in respect of the purity and yield of the product obtained or in respect of the high temperatures to be used or the inconvenience of the process, for example when additives which have to be separated off subsequently are used.

A process for the preparation of hydroxydiphenyls of the formula

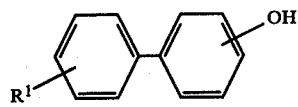

in which
R¹ denotes hydrogen or hydroxyl, by reacting diphenylsulphonic acids of the formula

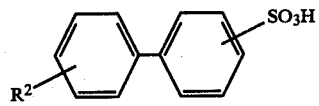

in which R² denotes hydrogen or the sulphonic acid group, or their alkali metal salts, with an alkali metal hydroxide at elevated temperature and elevated pressure, in the presence of water, has now been found, which is characterized in that 3 to 25 mols of aqueous alkali metal hydroxide having a concentration of at least 50% by weight are employed per equivalent of sulphonate group, at a temperature between 280 and 330° C. and an elevated pressure of up to 120 bar.

The process according to the invention is carried out at a temperature between 280° and 330° C., preferably at 300° to 325° C.

In accordance with the invention, the reaction is carried out at a pressure of up to 120 bar, for example 2 to 120 bar, preferably at 5 to 80 bar, particularly preferably at 10 to 40 bar. These pressures can be the autogenous pressure of the reaction mixture, or can be increased additionally to the autogenous pressure by forcing in an inert gas, for example nitrogen. The autogenous pressure of the reaction mixture is dependent, in a manner familiar in principle to the skilled worker, on the mixed ratios and concentration ratios in the reaction mixture and the reaction temperature set. This dependence applies in particular to the proportion of water in the reaction mixture. In the case in which a pressure in the lower part of the ranges mentioned is to be established, this can therefore be effected by blowing off steam from the reaction mixture via a pressure-regulating valve.

Examples of aqueous alkali metal hydroxides which may be mentioned are aqueous solutions of sodium hydroxide or potassium hydroxide, preferably sodium hydroxide, with a concentration of at least 50% by weight of alkali metal hydroxide, relative to the total weight of the aqueous solution. A concentration from 50 to 96% by weight, preferably from 60 to 95% by weight, particularly preferably 65 to 85% by weight, may be mentioned as an example. In this case, the amount of aqueous alkali metal hydroxide is such that 3 to 25 mols of alkali metal hydroxide, preferably 5 to 12 mols of alkali metal hydroxide, per equivalent of sulphonate group are present in the reaction mixture. The stated molar amounts of alkali metal hydroxide are relative in this case to equivalents of sulphonate groups, the sodium or the potassium salt of a diphenylsulphonic acid of the formula (II) being mentioned as an example of these.

Diphenylsulphonic acids of the formula (II) are prepared in a known manner, by sulphonating diphenyl with oleum or sulphuric acid (Liebigs Annalen der Chemie, 207 (1881), 320, in particular page 336; and U.S. 2,368,361). The sulphonic acids of the formula (II) which are obtainable in this reaction are then neutralized in a known manner to give the corresponding sulphonates. This neutralization can take place outside the reaction mixture for the process according to the invention so that an already neutralized sulphonate is employed in the process according to the invention. However, the neutralization to give the sulphonate can also take place in the process according to the invention, so that a free sulphonic acid of the formula (II) is employed in the process according to the invention. In accordance with the invention, it is furthermore possible to employ the sulphonic acid of the formula (II) or its alkali metal salts in dry or water-moist form or in the form of its aqueous solution. In accordance with the invention, it is therefore possible to apply either pure sulphonic acids of the formula (II) or sulphonating mixtures which contain such sulphonic acids of the formula (II) in addition to sulphuric acid which has not yet reacted and/or if desired in addition to SO₃ which has not yet reacted. The lastmentioned variant of the process according to the invention using sulphonating mixtures which have not yet been worked up, is preferred.

Since, in accordance with the invention, the molar amount of aqueous alkali metal hydroxide is relative to the equivalents of sulphonate groups, it is necessary, when free sulphonic acids are employed or when sulphonating mixtures containing such sulphonic acids are employed, to add an additional amount of alkali metal hydroxide sufficient for complete neutralization of all acidic groups present.

The following may be mentioned as examples of sulphonic acids of the formula (II) for the process according to the invention: 4-diphenylmonosulphonic acid, 2-diphenylmonosulphonic acid, 3-diphenylmonosulphonic acid, 4,4'-diphenyldisulphonic acid, 3,4'-diphenyldisulphonic acid and 3,3'-diphenyldisulphonic acid, preferably 4-diphenylmonosulphonic acid and 4,4'-diphenyldisulphonic acid.

The process according to the invention can be carried out, for example, as follows:

A highly concentrated aqueous solution of an alkali metal hydroxide is initially introduced into an autoclave, and the moist or dry alkali metal salt of a diphenylmonosulphonic acid or of a diphenyldisulphonic acid, or an aqueous solution of such an alkali metal salt, is gradually introduced. The autoclave is then closed and heated to a high temperature. As a result, the reaction mixture reacts in accordance with the invention. In general, 3 to 25 hours are required for the reaction. After the reaction is complete, the melt is cooled, and taken up in water. To prepare the free hydroxydiphenyl or dihydroxydiphenyl, the reaction mixture is acidified with a mineral acid, for example hydrochloric acid.

In a particular embodiment, the process according to the invention is characterized in that (a) an industrial diphenylsulphonic acid or diphenyldisulphonic acid mixture which contains sulphuric acid and if desired water and which contains at least 80% by weight of diphenylsulphonic acid or diphenyldisulphonic acid, relative to the total organic constituents present, and 1 to 60% by weight of sulphuric acid and if desired 3 to 30% by weight of water, relative to the total mass of the sulphonating mixture, is employed in the reaction, (b) this mixture, if desired as an aqueous solution, is mixed, at elevated temperature and if desired elevated pressure, with an amount of at least 50% strength by weight aqueous alkali metal hydroxide such that, after neutralization of the sulphuric acid and the total sulphonic acid groups, 3 to 25 mols of alkali metal hydroxide are present per equivalent of sulphonate group, (c) this alkaline reaction mixture is reacted at temperatures in the range between 280 and 330° C. and at a pressure of up to 120 bar, and (d) a mineral acid is added to the alkaline reaction mixture, if desired after it has been diluted with water, until a pH value of less than 8 is obtained, and the hydroxydiphenyl of the formula (I) is isolated at a temperature of, for example, $-5°$ C. to $+100°$ C.

The industrial sulphonating mixtures which can be employed according to the invention can, for example, have the following composition:

1. Example of an industrial diphenyl-4,4'-disulphonic acid mixture:

At least 30% by weight, for example 30 to 80% by weight, of diphenyl-4,4'-disulphonic acid, 0 to 8% by weight of diphenyl-3,4'-disulphonic acid, 0 to 5% by weight of diphenyl-3,3'-disulphonic acid, 0 to 2% by weight of diphenyl-4-sulphonic acid, 0 to 54% by weight of sulphuric acid and 20 to 1% by weight of water.

2. Example of an industrial diphenyl-4-sulphonic acid mixture:

At least 4.5% by weight, for example 4.5 to 80% by weight, of diphenyl-4-sulphonic acid, 0 to 5% by weight of diphenyl-2-sulphonic acid, 0 to 15% by weight of diphenyl 4,4'-disulphonic acid, 0 to 1% by weight of diphenyl, 15 to 0.5% by weight of sulphuric acid and 5 to 74% by weight of water.

These industrial sulphonating mixtures can, if desired, be diluted with up to an equal number of parts of water and then employed according to the invention. Such industrial diphenyl-4-sulphonic acid or diphenyl-4,4'-disulphonic acid mixtures can, for example, be prepared in the manner described above, by sulphonating diphenyl with sulphuric acid, which may contain water or free SO$_3$, at an elevated temperature.

Using the process according to the invention, it is possible to employ sulphonating mixtures, such as, for example, those mentioned above, directly and without intermediate isolation of the diphenyl-4-sulphonic acid or the diphenyl-4,4'-disulphonic acid or their alkali metal salts.

In the case of the diphenyl-4,4'-disulphonic acid, it can also be advantageous to separate off a part of the excess sulphuric acid beforehand from the sulphonating mixture, for example by diluting the sulphonating mixture with water and isolating the precipitated diphenyl-4,4'-disulphonic acid in the form of a paste containing only a small amount of sulphuric acid and organic by-products, for example by filtration.

In the case of the diphenyl-4-sulphonic acid, it can be advantageous if the unreacted diphenyl is wholly or partially separated off, for example by means of steam distillation, from the sulphonating mixture after the latter has been diluted with water.

When a sulphonating mixture is employed according to the invention, it can be used without intermediate cooling, at the temperature of the preceding sulphonation reaction, in the reaction, according to the invention, with aqueous alkali metal hydroxide. In this procedure, the total amount of heat present in the sulphonating mass is introduced into the process step according to the invention, so that the energy which must otherwise be applied to heat and melt the organic component can be saved. Furthermore, when the industrial sulphonating mixture is mixed directly with the aqueous alkali metal hydroxide, an additional amount of heat from the neutralization reaction of the sulphuric acid and the sulpho groups is introduced into the reaction mixture of the process according to the invention, resulting in an extremely economical process for the preparation of hydroxydiphenyl of the formula (I).

This is surprising because in all processes disclosed hitherto the intermediate isolation of the diphenyl-mono- or diphenyl-disulphonic acid in the form of its alkali metal salt was thought to be necessary since this salt, as a solid, can be mixed with the alkali metal hydroxide in a simple manner, and since a purification, which was thought to be necessary, is carried out simultaneously in the intermediate isolation. In this purification, which was thought to be necessary, in particular sulphuric acid from the excess sulphonating reagent, and a part of the by-products which are unavoidable in any sulphonation by an economical sulphonation process, for example isomeric diphenylsulphonic acids, and other organic by-products which remain in solution when purification is carried out in the mother liquor are removed.

The preferred variant of the process according to the invention, using sulphonating mixtures described by way of example, accordingly shows the following advantages:
(a) the additional process step of the formation of alkali metal salts of sulphonic acids can be dispensed with;
(b) the supply and subsequent evaporation of large amounts of water which operations are necessary for the intermediate isolation and drying of such alkali metal salts, and the associated outlay of energy, can be dispensed with;
(c) the substantial amounts of diphenylsulphonic acid which remain in the mother liquors in conventional purification processes for the intermediate isolation of the alkali metal salts mentioned remain in the process and thereby increase the total yield;
(d) in intermediate isolation processes according to the prior art, waste water effluents result which, in the case of partial neutralization and in particular in the case of salting-out of such alkali metal salts with sodium chloride, contain substantial amounts of sulphuric acid (dilute acid); such waste water effluents are prevented according to the invention;
(e) the abovementioned heat energies which are present in the crude sulphonating mixture are retained.

The mixing of the industrial sulphonating melts of diphenylsulphonic acids, which melts have been mentioned as examples, with the water-containing alkali metal hydroxide can be effected in various ways in order to keep the abovementioned amounts of heat in the reaction system and to utilize the advantageously:

1. The undiluted industrial diphenylsulphonic acid sulphonating melt is, for example, metered into initially introduced aqueous sodium hydroxide solution which has been heated to the boiling point and has the abovementioned concentration, water being distilled off continuously without the external supply of heat, and the mixture being concentrated thereby. Such a water distillation can, however, also follow the pre-mixing.
2. The diphenylsulphonic acid sulphonating melt is pumped or pressed, under pressure, into initially introduced molten aqueous sodium hydroxide solution of the concentration given above, the reaction temperature as mentioned above, which is favourable for the subsequent reaction to give the hydroxydiphenyl of the formula (I), being reached solely by utilizing the amounts of heat liberated in this procedure. If in this process variant it is intended to limit the pressure, which increases simultaneously, this can be effected by blowing off steam via a pressure-regulating valve.
3. The undiluted industrial sulphonating melt and aqueous alkali metal hydroxide are pumped simultaneously into a mixing tube, the mixing tube being of a design such that complete mixing is effected solely by the turbulent flow which results. If desired, the mixing can also be supported by baffles in the mixing tube, but this measure is not absolutely necessary. For example, 2,000 to 5,000 ml of industrial sulphonating melt can be mixed with the appropriate amounts of aqueous sodium hydroxide solution in one hour in a mixing tube of 500 mm length and 5 mm diameter, and fed into a reaction vessel. When the starting temperatures of the components to be mixed are suitably chosen, for example 90° C. to 130° C. for the sulphonating melt and 80° C. to 110° C. for the sodium hydroxide solution, a reaction temperature between 280° C. and 330° C., which is favourable for the reaction to give the hydroxydiphenyl of the formula (I), is reached at the end of the mixing tube. As a result of this, the reaction to give the hydroxydiphenyl of the formula (I) can, if necessary, already be carried out at least partially in this mixing tube. However, it may also be advantageous to carry out the mixing at a lower temperature, and to limit the resulting steam pressure by blowing off steam in the manner described. This process is thus a partially continuous process, in which the mixing in the mixing tube represents the continuous part of the process, and the subsequent completion of the reaction in an autoclave represents the discontinuous part.

The working-up and isolation of the free hydroxydiphenyl of the formula (I) are effected according to customary methods, for example by adding a strong mineral acid, for example hydrochloric acid or sulphuric acid, unit a pH value of less than 8, preferably 6.5 to 7.5, is reached. Thereafter, the mixture obtained can be diluted with an amount of water required to dissolve the inorganic salts, and the desired hydroxydiphenyl can be precipitated in high purity. For this precipitation, the temperature is adjusted, for example, to about $-5°$ C. to about $+100°$ C.

In the process according to the invention, the hydroxydiphenyls of the formula (I) are obtained in high yield and in high purity.

EXAMPLE 1

3,161 g of aqueous 81% strength sodium hydroxide solution (64 mols) were initially introduced into an Inconel autoclave, and 1,005 g of 100% (3.2 mols) diphenyldisulphonic acid, as the sodium salt, were introduced while stirring. The autoclave was pressure-sealed and kept at 320° C. for 15 hours. A pressure of 8-15 bar was established. After the reaction time had elapsed, the mixture was allowed to cool to 280° C. and approx. 1,000 ml of water were pumped in. After the mixture has been cooled, the suspension was removed from the autoclave. The autoclave was rinsed with water, and the total mixture was made up to 7 liters with water. To isolate the 4,4'-dihydroxydiphenyl, the mixture was neutralized to a pH value of 7-7.5 by the addition of 30% strength hydrochloric acid. The precipitated product was filtered off under suction and washed with water. The moist product obtained was dried in vacuo at 100° C. Purification was effected by sublimation.

Analysis (by gas chromatography): 98.8–99.0% of 4,4'-dihydroxydiphenyl, 0.9–1.2% of m- and p-phenylphenol.

Yield of 4,4'-dihydroxydiphenyl sublimated: 96% of the theoretical yield.

EXAMPLE 2

3,161 g of aqueous 81% strength sodium hydroxide solution (64mols) were initially introduced into an Inconel autoclave, and 749 g of 100% (3.2 mols) diphenyl-4-sulphonic acid, as the sodium salt, were introduced while stirring. The autoclave was pressure-sealed, and kept at 320° C. for 15 hours. A pressure of 8-15 bar was established. After the reaction time had elapsed, the mixture was allowed to cool to 280° C., and the reaction mixture was worked up as in Example 1.

Analysis (by gas chromatography): 99.5–99.6% of 4-hydroxydiphenyl, 0.2% of 4,4'-dihydroxydiphenyl Solidification point: 164–164.2° C.

Yield of 4-hydroxydiphenyl sublimated: 97% of the theoretical yield.

EXAMPLE 3

693 g of aqueous 75% strength sodium hydroxide solution (=13 mols) were initially introduced into a 1.3 litre nickel autoclave, at 110° C.

At the same time, 479 g of diphenyl-4,4'-disulphonic acid sulphonating mixture (1.05 mols of diphenyl 4,4'-disulphonic acid) of the following composition: 68.7% by weight of diphenyl-4,4'-disulphonic acid, approx. 0.5% by weight of diphenyl-3,4'-disulphonic acid, 0.05% by weight of diphenyl-4-monosulphonic acid, 5.8% by weight of H₂SO₄ and 25.0% by weight of H₂O were melted at 90° C. in a VA stainless steel autoclave, and were forced via a heated line, in the course of approx. 30 seconds, under the surface of the thoroughly stirred sodium hydroxyide solution, using nitrogen at 20 bars. The temperature in the nickel autoclave increased to 186° C. and the pressure increased to 22 bar. Subsequent analysis showed that 0.99 mol of the sulphonating melt had been brought to reaction in this process. The reaction mixture was heated to 320° C., and stirred for a further 14 hours at this temperature. The autogenous pressure, raised by the additional N₂ pressure, increased to 64 bar. After the reaction mixture had cooled to 200° C., 400 ml of water were pumped into it. After further cooling to 20° C., a pale, fine-grained, readily stirrable suspension was obtained, the composition of which was analysed by means of high pressure liquid chromatography.

The suspension contained: 169.5 g of 4,4'-dihydroxydiphenyl=92% of the theoretical yield, relative to diphenyl-4,4'-disulphonic acid forced in, and 2.3 g of 4-hydroxy-diphenyl.

The working-up was effected as in Example 1. 169.9 g of 98.8% strength 4,4'-dihydroxydiphenyl, =91% of the theoretical yield, were obtained. The product contained 1.2% by weight of 4-hydroxydiphenyl.

EXAMPLE 4

775 g of 80% strength aqueous sodium hydroxide solution (=15.5 mols) were initially introduced into a 1.3 litre nickel autoclave. 408 g of diphenyl-4,4'-disulphonic acid sulphonating mixture (0.5 mol of diphenyl-4,4'-disulphonic acid) which had the following composition: 38.5% by weight of diphenyl-4,4'-disulphonic acid, approx. 1.0% by weight of diphenyl-3,4'-disulphonic acid, approx. 0.2% by weight of diphenyl-3,3'-disulphonic acid, 0.05% by weight of diphenyl-4-monosulphonic acid, 55.8% by weight of H₂SO₄ and 4.5% by weight of H₂O, and which had been heated to 120° C., were pumped into the autoclave. The temperature increased to approx. 325° C. and the pressure increased to 40 bar. The reaction mixture was stirred for a further 14 hours at 325° C., cooled to 200° C., diluted with 400 ml of water, cooled to 20° C. and diluted with water to a volume of approx. 3 litres, until a solution was formed. The solution was adjusted to a pH value of 7 by the addition of approx. 410 g (4.2 mols) of 100% strength by weight H₂SO₄, the suspension was cooled to 20° C., and the precipitated 4,4'-dihydroxydiphenyl was filtered, washed with approx. 1,000 ml of water and dried in vacuo at 60° C. 73.5 g of 96.5% strength 4,4'-dihydroxydiphenyl=92% of the theoretical yield, relative to diphenyl-4,4'-disulphonic acid, were obtained. The product contained 1.3% by weight of 4-hydroxy-diphenyl.

WHAT IS CLAIMED IS:

1. In a process for the preparation of a hydroxydiphenyl or an alkali metal diphenylate of the formula

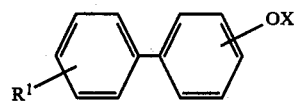

in which
X=hydrogen or an alkali metal
R¹ denotes hydrogen or hydroxyl by contacting a diphenylsulphonic acid of the formula

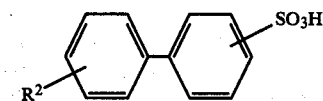

in which
R² denotes hydrogen or the sulphonic acid group, or their alkali metal salts, with an alkali metal hydroxide at elevated temperature and elevated pressure in the presence of water,
the improvement wherein the process is carried out employing 3 to 25 mols of aqueous alkali metal hydroxide having a concentration of at least 50% by weight per equivalent of sulphonate group, at a temperature between 280 and 330° C. and at an elevated pressure of up to 120 bar and, in the case that X denotes hydrogen treating the obtained diphenylate with a mineral acid.

2. A process according to claim 1, wherein the process is carried out a temperature of 300° to 325° C.

3. A process according to claim 1, wherein the process is carried out at a pressure of 5 to 80 bar.

4. A process according to claim 3, wherein the process is carried out at a pressure of 10 to 40 bar.

5. A process according to claim 3, wherein the process is carried out employing an aqueous alkali metal hydroxide solution of 50 to 85% by weight alkali metal hydroxide.

6. A process according to claim 1, wherein the aqueous alkali metal hydroxide solution contains 5 to 21 mols of alkali metal hydroxide per equivalent of sulphonate group.

7. A process according to claim 1, wherein the alkali metal hydroxide is sodium hydroxide.

8. A process according to claim 1, wherein following reaction of the diphenyl sulphonic acid or its alkali metal salt with the aqueous alkali metal hydroxide solution, the free hydroxy diphenyl is formed by adding a mineral acid thereto until the pH drops to a value of less than 8.

9. A process according to claim 8, wherein following addition of said mineral acid, the free hydroxy diphenyl is isolated from the reaction mixture at a temperature of −5 to +100° C.

10. A process according to claim 9, wherein the diphenyl sulphonic acid or its alkali metal salt is in the form of an industrial sulphonating mixture which contains, in addition to 1 to 60° by weight of sulphuric acid, at least 80% by weight of disulphonic acids of said formula, relative to the weight of the total organic constituents present and an amount of alkali metal hydroxide is added to such mixture such that, after neutralization of all acid groups present, 3 to 25 mols of alkali metal hydroxide per equivalent of sulphonate group are present.

11. A process according to claim 10, wherein in addition to 1 to 60% by weight of sulphuric acid being present in said industrial sulphonating mixture, there is also present 3 to 30% by weight water.

12. A process according to claim 10, wherein said industrial sulphonating mixture is pumped, under pressure, into an initially introduced aqueous alkali metal hydroxide solution and the preparation of the hydroxy diphenyl or alkali metal diphenylate is carried out utilizing the amounts of heat liberated by addition of said industrial sulphonating mixture to said initially introduced aqueous alkali metal hydroxide.

13. A process according to claim 10, wherein said industrial sulphonating mixture and said aqueous alkali metal hydroxide are mixed in a mixing tube.

14. A process according to claim 13, wherein said industrial sulphonating mixture and said aqueous alkali metal hydroxide are at least partially reacted in said mixing tube.

15. A process according to claim 1, wherein $R^2$ denotes a sulphonic acid group.

16. A process according to claim 1, wherein $R^2$ denotes hydrogen.

17. A process according to claim 1, wherein the diphenylsulphonic acid which is reacted with the alkali metal hydroxide is in the form of its alkali metal salt.

18. A process according to claim 1, wherein said diphenylsulphonic acid is selected from the group consisting of 4-5, monosulphonic acid, 2-diphenylmonosulphonic acid, 3-diphenylmonosulphonic acid, 4-4'-diphenyldisulphonic acid, 3,4'-diphenyldisulphonic acid and 3,3'-diphenyldisulphonic acid.

19. A process according to claim 1, wherein said aqueous alkali metal hydroxide solution is reacted with an industrial diphenyl-4,4'disulphonic acid mixture comprising 3 to 80% by weight of diphenyl-4,4'disulphonic acid, 0 to 8% by weight of diphenyl-3,4'disulphonic acid, 0 to 5% by weight of diphenyl-3,3'disulphonic acid, 0 to 2% by weight of diphenyl-4-sulphonic acid, 0 to 54% by weight of sulfuric acid and 1 to 20% by weight of water.

20. A process according to claim 1, wherein said aqueous alkali metal hydroxide solution is reacted with an industrial diphenyl-4-sulphonic acid mixture comprising 4.5 to 80% by weight of diphenyl-4-sulphonic acid, 0 to 5% by weight of diphenyl-2-sulphonic acid, 0 to 15% by weight of diphenyl-4,4'-disulphonic acid, 0 to 1% by weight of diphenyl, 0.5 to 15% by weight of sulfuric acid and 5 to 74% by weight of water.

21. A process according to claim 1, wherein the process is carried out at a pressure of at least 2 bars.

22. A process according to claim 1, carried out in the absence of a metal phosphate.

* * * * *